(12) United States Patent
Ikhlef et al.

(10) Patent No.: US 7,455,454 B2
(45) Date of Patent: Nov. 25, 2008

(54) X-RAY DETECTOR METHODS AND APPARATUS

(75) Inventors: Abdelaziz Ikhlef, Versailles (FR); Naveen Stephan Chandra, Kenosha, WI (US)

(73) Assignee: General Electric Company, Schenectady, NY (US)

( * ) Notice: Subject to any disclaimer, the term of this patent is extended or adjusted under 35 U.S.C. 154(b) by 160 days.

(21) Appl. No.: 11/542,081

(22) Filed: Oct. 3, 2006

(65) Prior Publication Data

US 2008/0080665 A1    Apr. 3, 2008

(51) Int. Cl.
*G01D 18/00* (2006.01)

(52) U.S. Cl. .................. 378/207; 250/370.15

(58) Field of Classification Search .................. 378/19, 378/98.8, 207; 250/370.15
See application file for complete search history.

(56) References Cited

U.S. PATENT DOCUMENTS

| 4,967,082 | A | | 10/1990 | Cooke et al. ............. 250/338.3 |
| 5,644,610 | A | * | 7/1997 | Crawford et al. .............. 378/19 |
| 5,955,793 | A | * | 9/1999 | Khadkikar et al. .......... 307/117 |
| 6,828,563 | B2 | | 12/2004 | Ducourant ............ 250/370.11 |
| 2005/0018810 | A1 | * | 1/2005 | Narayanaswamy et al. ... 378/91 |
| 2005/0287008 | A1 | * | 12/2005 | Lacey et al. ................... 417/32 |

* cited by examiner

*Primary Examiner*—Chih-Cheng G Kao
(74) *Attorney, Agent, or Firm*—Fisher Patent Group, LLC; Thomas M. Fisher (57) ABSTRACT

A method includes creating a lookup table for thermal correction of a x-ray detector on a pixel by pixel basis.

8 Claims, 9 Drawing Sheets

X-RAY DETECTOR METHODS AND APPARATUS

BACKGROUND OF THE INVENTION

This invention relates generally to diagnostic imaging methods and apparatus, and more particularly, to methods and apparatus that provide for thermal gain management and correction in the detector for computed tomography in particular and in medical imaging in general.

Most multi-slices computed tomography (CT) scanners are built with detectors composed of scintillator/photodiodes arrays. The photodiodes arrays are mainly based on front-illuminated technology. However, new designs based on back-illuminated photodiodes (backlit diodes) are being investigated for CT machines to overcome the challenge of the higher number of runs and connections required. Current CT detectors generally use scintillation crystal/photodiode arrays, where the scintillation crystal absorbs x-rays and converts the absorbed energy into visible light. A photodiode is used to convert the light to an electric current. The electric current is read and the reading is proportional to the total energy absorbed.

A CT detector should meet tight performance requirements in order to enable the generation of high quality and artifact free CT images. First, the detector should provide a response that is linearly related to x-ray intensity. Some of the requirements on the detector that result from this are the stability of the detector over time and temperature, the non-sensitivity to focal spot motion, and a bound on the light output variation over life, etc. In a third generation CT scanner, the relative behavior of adjacent channels should be nearly identical in order to avoid serious ring artifacts (usually defined as channel to channel non-linearity variation) in images. This variation might be affected by the scintillator behavior from one pixel to its neighbor, by the collimator plate variations, and/or by the diode pixel response. Generally, if these requirements are not met, ring artifacts, bands and/or smudges/spots might appear in images.

One of the contributors of this channel to channel variation (or module to module variation) is the gain variation caused between photodiode pixels due to the variation of temperature. In Volume CT, with a relatively large coverage of the collimator, the variation of the temperature at the diode will be high and tight thermal control from calibration conditions to scanning conditions would be required. The thermal gain temperature coefficient drift in the module may have multiple root causes: a) diode, b) collimator, c) scintillator, d) DAS electronics and finally e) DAS assembly. To overcome this problem, one can either introduce very tight thermal control on the detector or compensate for the thermal drift by introducing a thermal calibration or correction. For this, an accurate measurement of the temperature on each pixel would be desirable.

BRIEF DESCRIPTION OF THE INVENTION

In one aspect, a method includes creating a lookup table for thermal correction of a x-ray detector on a pixel by pixel basis.

In another aspect, a method includes using a single diode for measuring the temperature of the diode and for receiving x-rays in the diode.

In another aspect a system is provided. The system includes an energy source, an energy detector positioned to receive energy emitted from the source, the energy detector including a plurality of diodes, and a computer coupled to the detector. The computer is configured to store a lookup table for thermal correction of the detector on a diode by diode basis.

BRIEF DESCRIPTION OF THE DRAWINGS

FIG. 1(a,b) shows the Current versus Voltage (IV) behavior of the VCT backlit diode versus temperature.

FIG. 3(a,b) shows the IV behavior of the VCT backlit diode versus temperature.

DETAILED DESCRIPTION OF THE INVENTION

There are herein described methods and apparatus useful for imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of an x-ray system, it is contemplated that the benefits of the invention accrue to all diagnostic imaging systems and modalities such as PET, MRI, SPECT, Ultrasound, fused systems such as a CT/PET system, and/or any modality yet to be developed in which detectors are used.

In this disclosure, methods and apparatus are described that will enable the measurement of the absolute temperature seen by each pixel in an array of diodes used in a multislice CT detector. The multislice CT detector element consists of an array of 16 cells in X-axis and 64 cells in the Z-axis for a VCT (volume computed tomography) detector. The measurement setup can however be extended to any diode system.

In the VCT detector, the use of Backlit (BL) diodes is desirable to make a wide z-coverage tile-able detector. One advantage of BL diodes is to more efficiently/effectively connect detector modules not only in the x-direction but also in the z-direction, and one of the disadvantages is that this design requires very tight control of the temperature at the diode level to avoid gain change due to temperature drift. This becomes even more critical when more than 64 slices are used, and when thinner slices are built. Currently, the temperature drift from calibration to imaging stations has to be maintained within a few degrees.

One can envision measuring the temperature of the pixel at which it has been calibrated and storing it in a look-up table for later use. Knowing the response of the diode-scintillator pixel at different temperatures would enable the correction of image quality drift due to temperature. This will enable at the same time the relaxation of the thermal management of both the detector and the gantry. The algorithm for gain correction can be determined later.

The challenge to make this correction possible is to find an innovative method to measure the temperature of the pixel before each scan and use the value for correction of the diode response. One way to achieve this is to use the detector diode as the sensor itself. This can be achieved by introducing the capability of forwarding or reversing the bias of the diodes and acquire the signal under no x-ray exposure (e.g. a dark current).

Measurement Principle: Semi-conductor Diodes are excellent sensing devices for temperature measurement at low values of forward current and using reverse bias mode current. At low forward current (Im), the junction temperature Tj of the diode correlates linearly with the junction forward voltage (Vf).

$$\Delta T_j = K \cdot \Delta V_f$$

where K is a factor with units C/mV, generally with 0.4 and 0.8 C/mV.

A change in the junction temperature produces a corresponding change in the forward voltage and consequently a change in the forward current. The diode in this case needs to be forward biased. The operation of the diode just below the threshold voltage, will lead to a better sensitivity of measurement as a function of temperature variation.

Another concept is to use the diode in the reverse bias mode and measure the dark current. It is known that the dark current is exponentially varying with temperature.

Whether forward biased or reverse biased, one can use the same diode for measuring the temperature and the x-ray signal, by switching back and forth between two modes. All pixels of the detector may be used or a subset of pixels may be used.

In CT detectors, the current generated in the diodes is measured using a digital to analog system (DAS) and it is possible to use the same DAS to measure the current under either forward biased or reverse biased conditions to deduce the temperature of that pixel.

Figure 1:
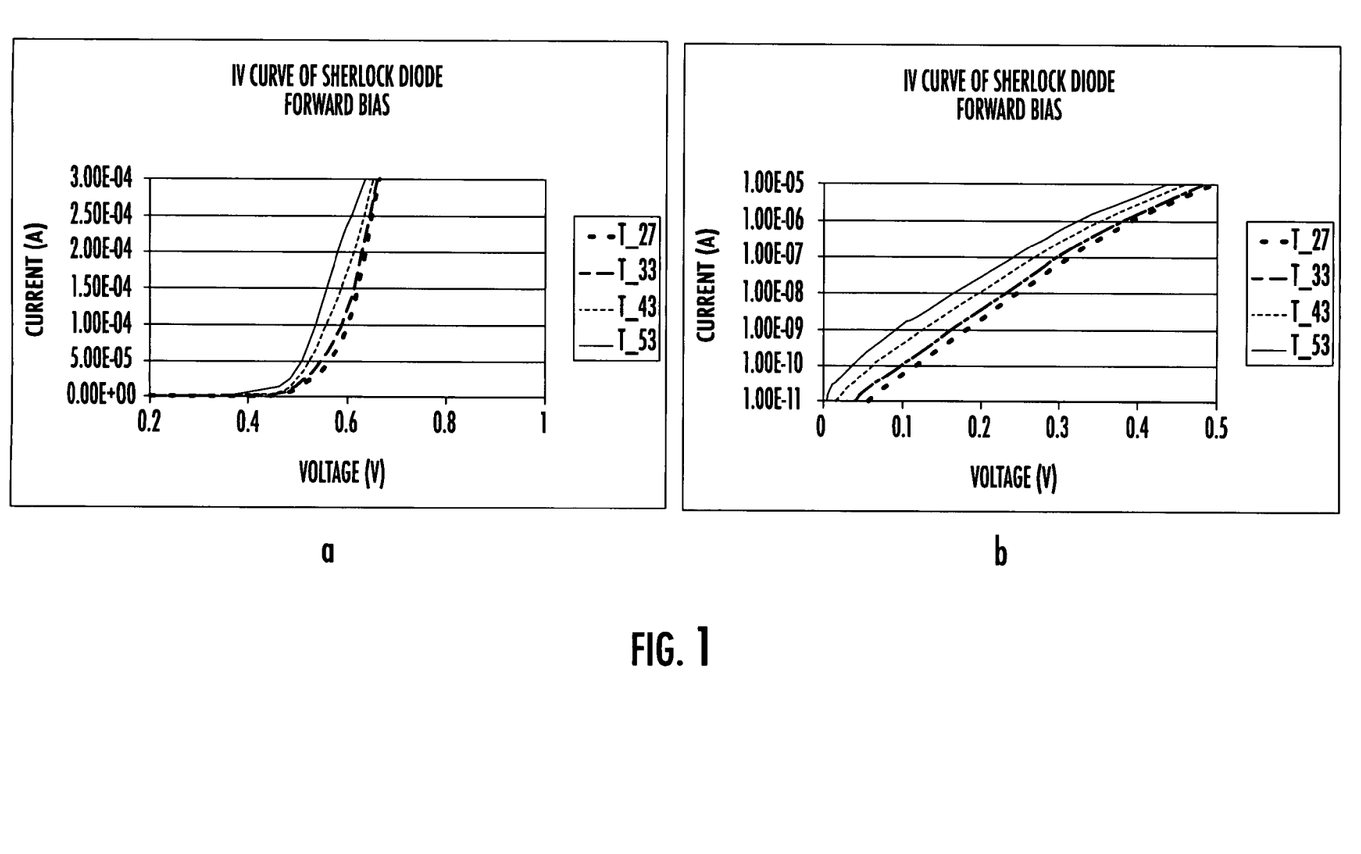
Figure 2:
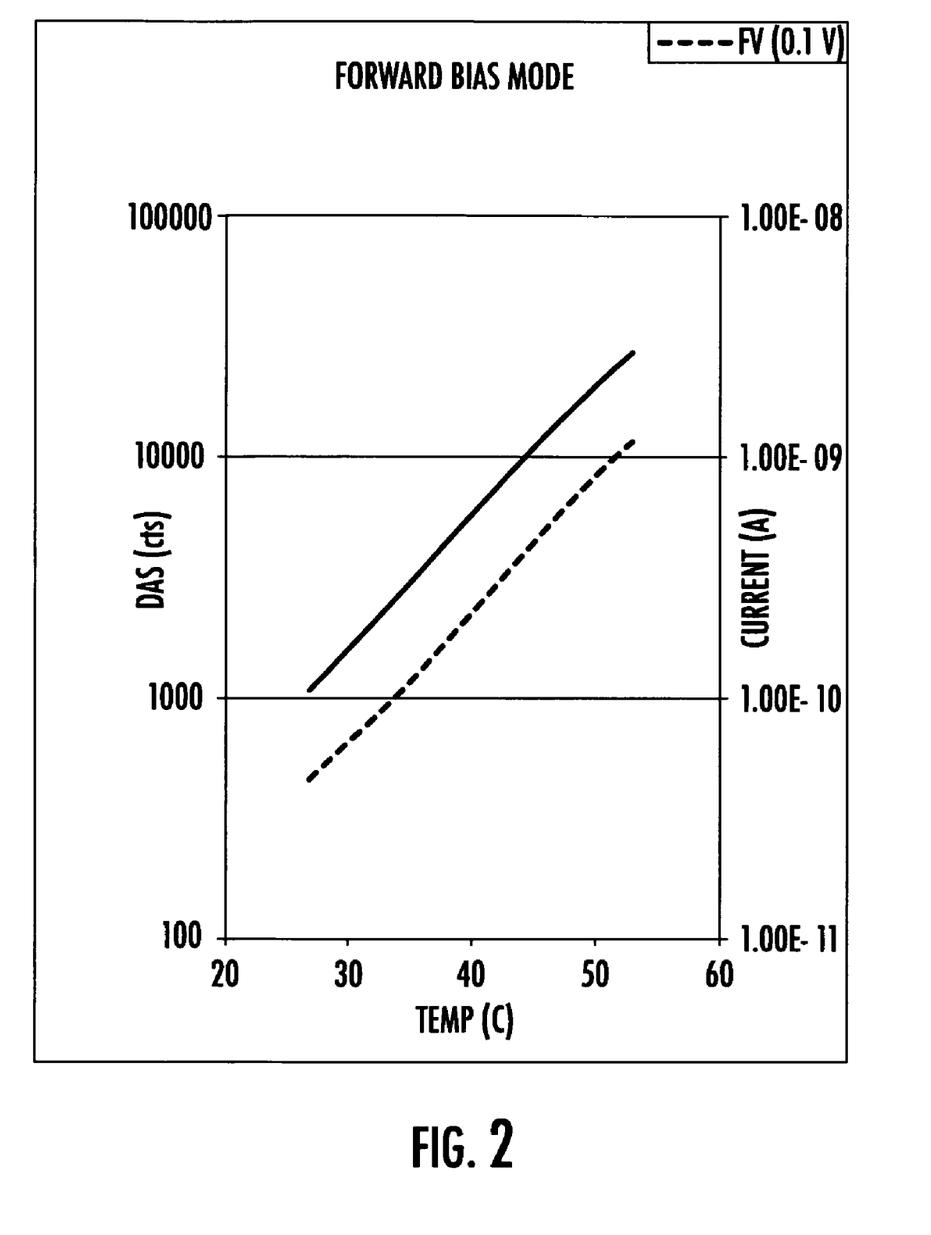
FIG. 2 shows the current produced by the diode as function of temperature.

Forward Bias Method: In this method, one can forward bias the diode just before starting the x-ray scan. One can read the current generated by the diode under forward biasing conditions using the DAS. FIG. 1 (a,b) shows the IV behavior of the VCT backlit diode versus temperature. FIG. 2 shows the current produced by the diode as function of temperature. The curve is described by an exponential function as predicted by theory.

Figure 3:
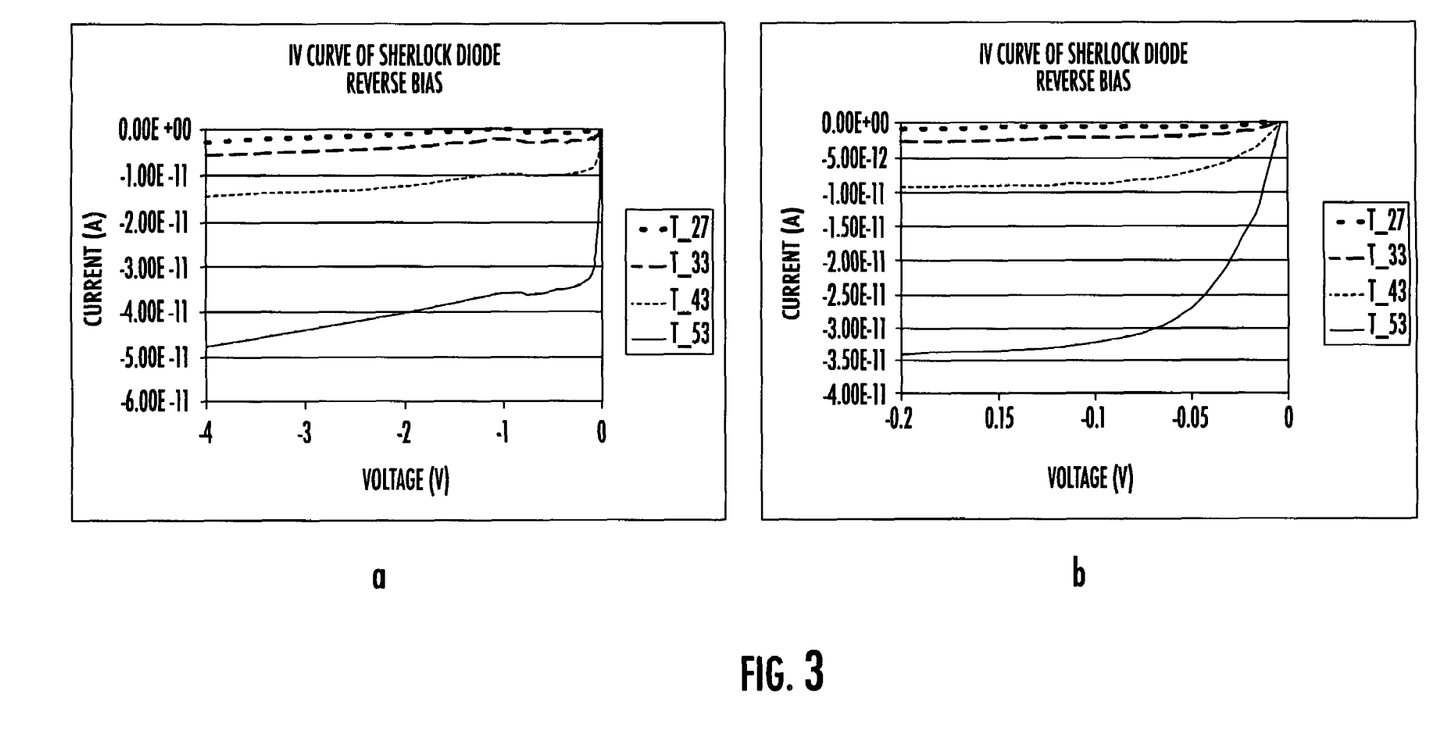
Figure 4:
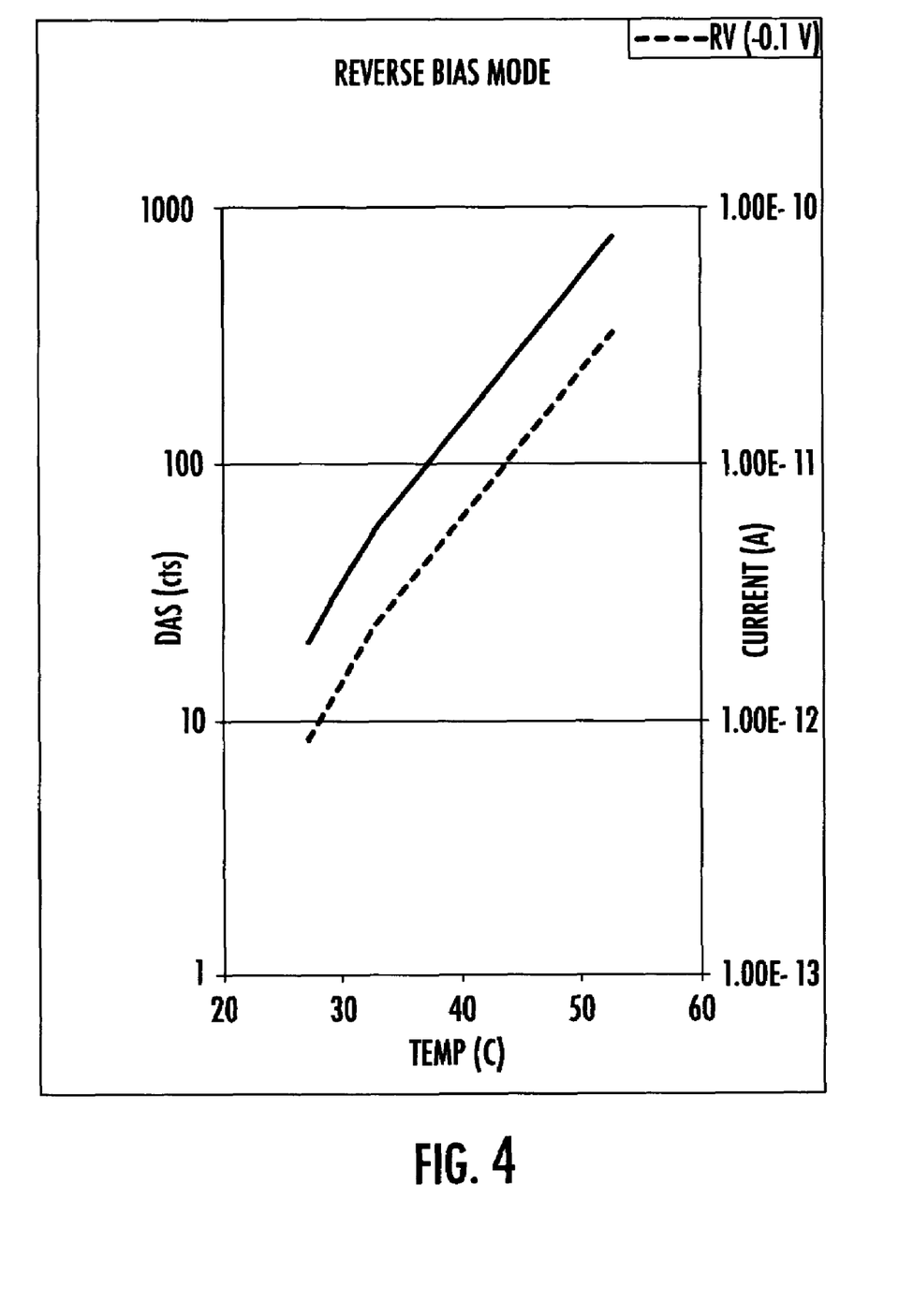
FIG. 4 shows the current produced by the diode as function of temperature.

Reverse Bias Method: In this method, one can reverse bias the diode just before starting the x-ray scan. One can read the dark current generated by the diode using the DAS. FIG. 3(a,b) shows the IV behavior of the VCT backlit diode versus temperature. FIG. 4 shows the current produced by the diode as function of temperature. The curve is described by an exponential function as predicted by theory.

Figure 5:
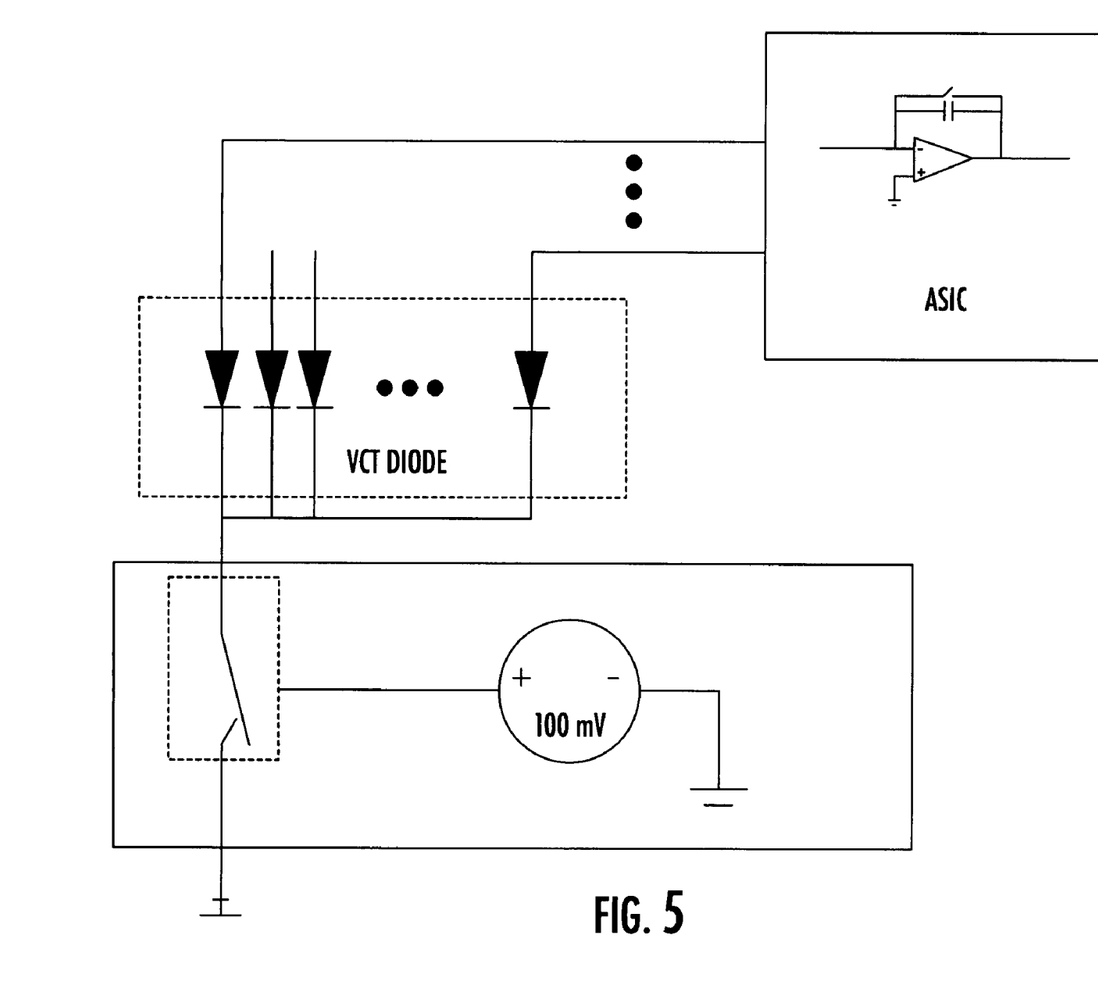
FIG. 5 illustrates an example of an incarnation to implement the biasing requiring electronic circuitry.
Figure 6:
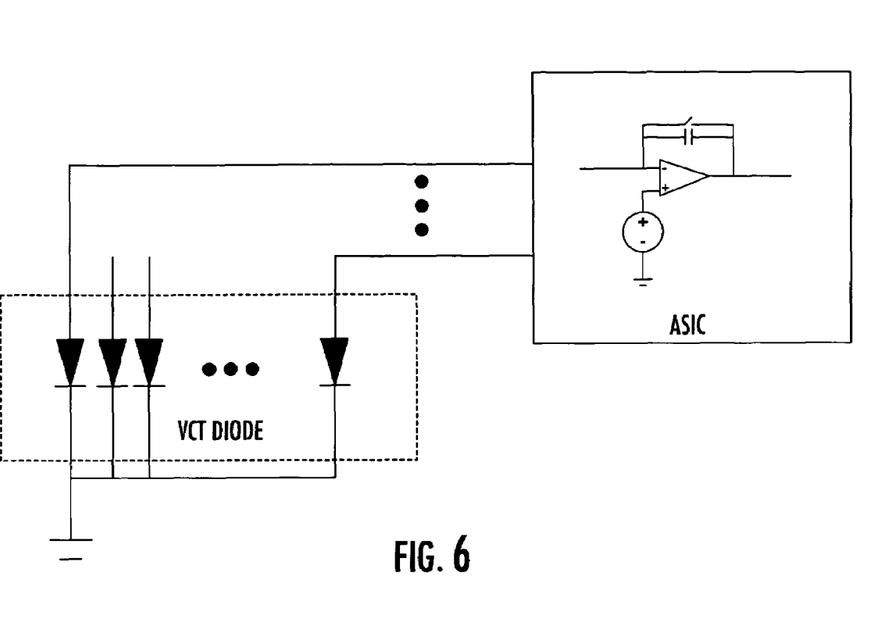
FIG. 6 shows the idea of using the non-inverting input of the DAS for the forward bias connection.

Circuit Diagram proposal: An example of how to bias the diode (forward or reverse) using electronic circuitry is shown in FIGS. 5 and 6. This circuit can easily reside on an A/D board. In the case presented one switch is sufficient to achieve this. During the temperature reading, the switch is connected to a bias voltage to reverse bias the diode and read the dark current. During the x-ray scan, the switch is closed and connected to ground, and x-ray signal can be read. By changing the polarity of the bias, the same scheme can be used for forward biased diodes as long as the DAS is capable of reading either positive or negative current (which is feasible for many DAS architectures).

A second case of forward bias implementation occurs when the DAS is not capable of reading negative current. In this case, the orientation of the diode needs to be reversed so that the current will flow from the diode to the amplifier. For this to happen, a high number of switches need to be added. Alternatively, one can forward bias the diode by supplying a voltage supply on the non-inverting input of the DAS. The anode side of the diode being connected on the inverting input of the DAS amplifier, will see the voltage connected on the non-inverting input, and cause current to flow accordingly.

Figure 7:
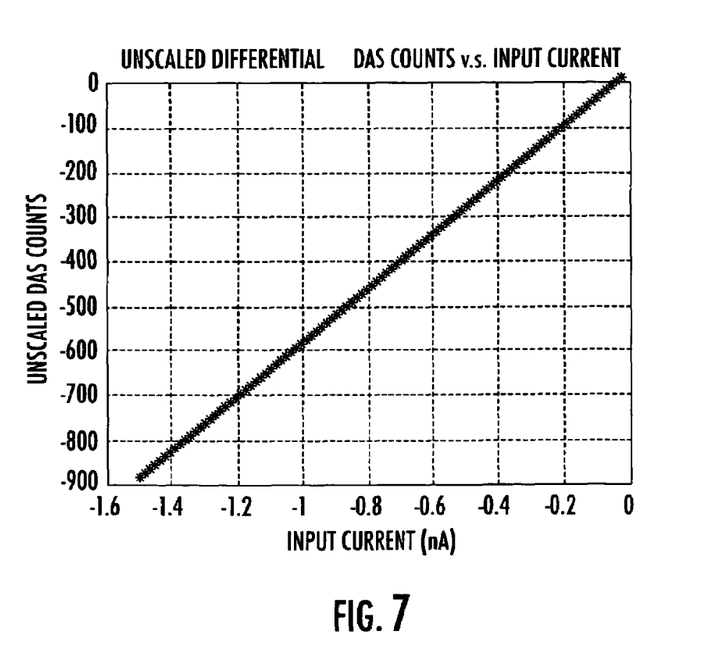
FIG. 7 shows the results of the current difference at different biases.

Temperature Measurement Algorithm: since in the real design, there is a DC component in the dark current measurement, which is independent of temperature, one can use a measurement of temperature using two points for correction. The first point would be at bias conditions (reverse or forward bias of the appropriately selected bias voltage, for example 100 mV) and the second at no-bias (0 volts—representing the unbiased state of the diode during x-ray exposure or scanning ). The difference should be described by a function, which is exponentially varying with temperature. The sensitivity can then be improved by optimizing the trigger rate in order to achieve the best resolution (variable trigger rate or fixed trigger rate), or by using a continuous integration time, or by averaging multiple acquisitions under the same conditions. FIG. 7 shows the results of the current difference at different biases. This curve shows only the effect of temperature on the dark current by removing the DC component.

Figure 8:
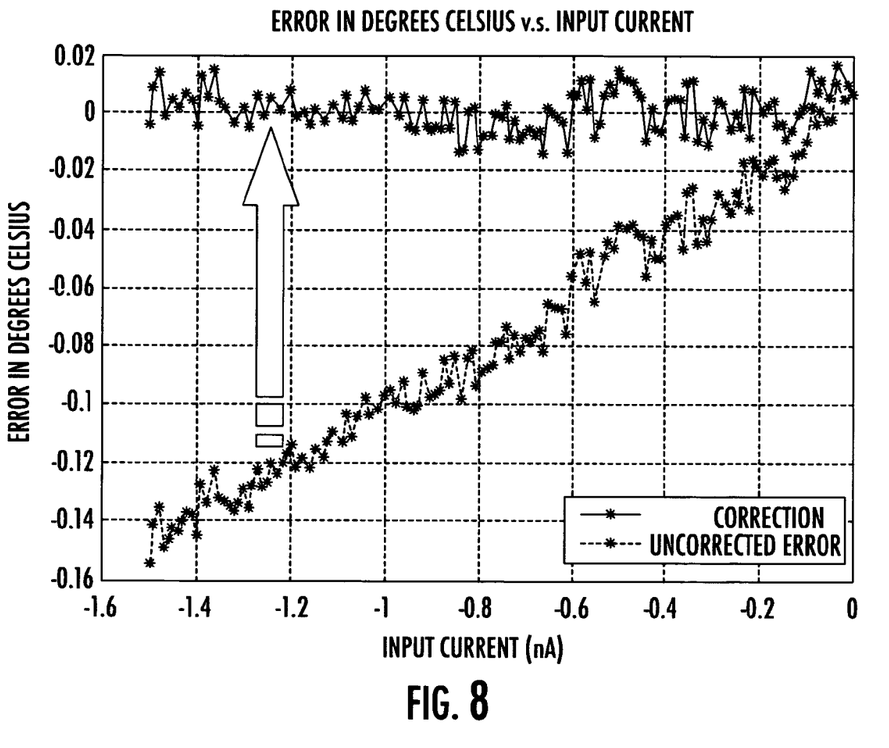
FIG. 8 shows the results of DAS based thermal gain correction vector, and its effects on DAS measurement accuracy.

In order to improve the accuracy of the DAS measurements, a DAS thermal gain correction scheme can be implemented which can improve the accuracy by an order of magnitude. The scheme can call for a one-time A/D board calibration resulting in a channel based gain vector that would get applied to all the differential measurements made by reverse biasing the diodes. This would have the effect of removing the DAS based channel to channel differences due to process variation. This correction can occur inside the DAS/Detector subsystem, or can reside on the CT System Host itself. FIG. 8 illustrates the effect of one such correction on the accuracy of the measurement.

Figure 9:
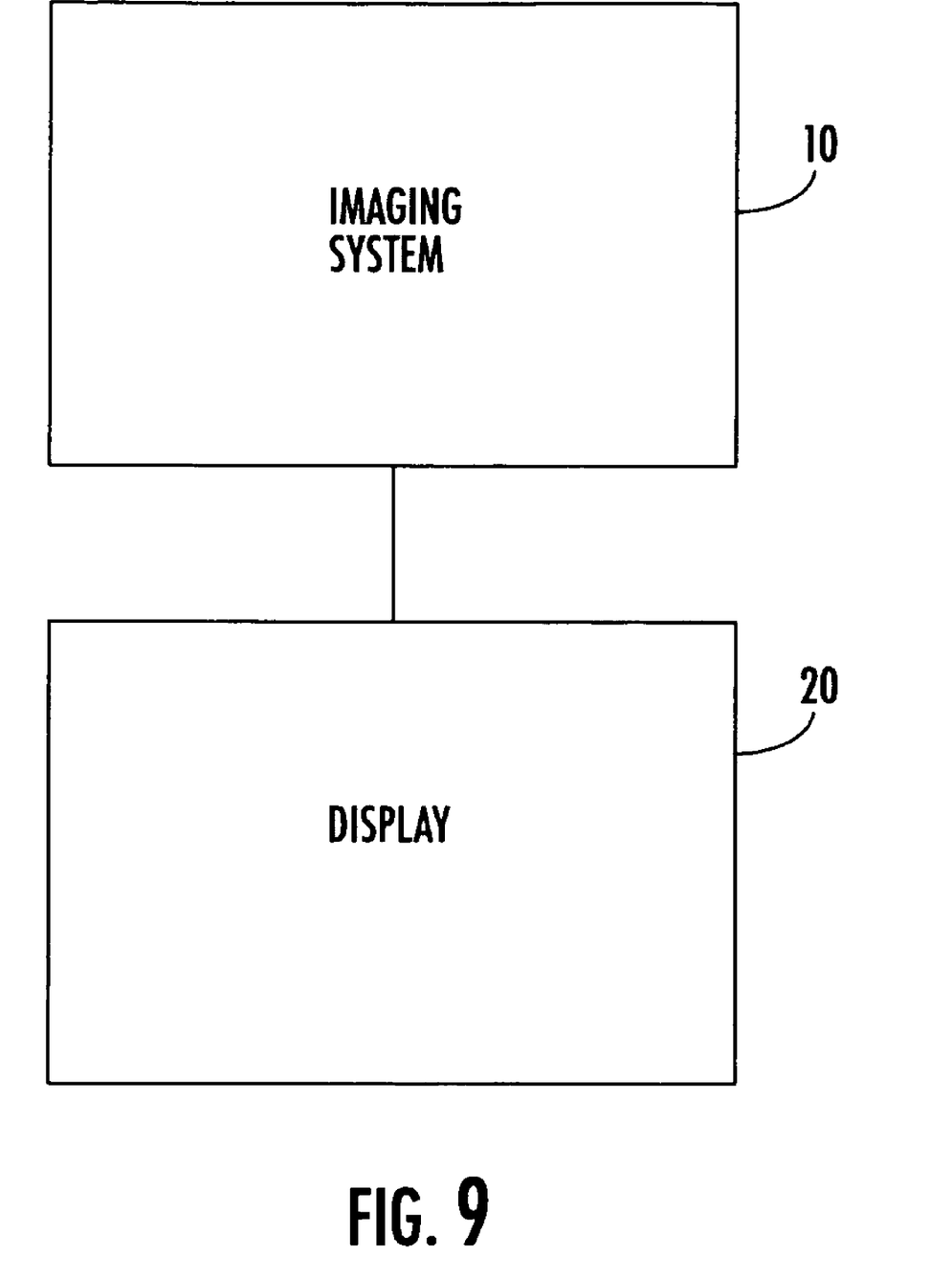
FIG. 9 illustrates an imaging system.
Figure 10:
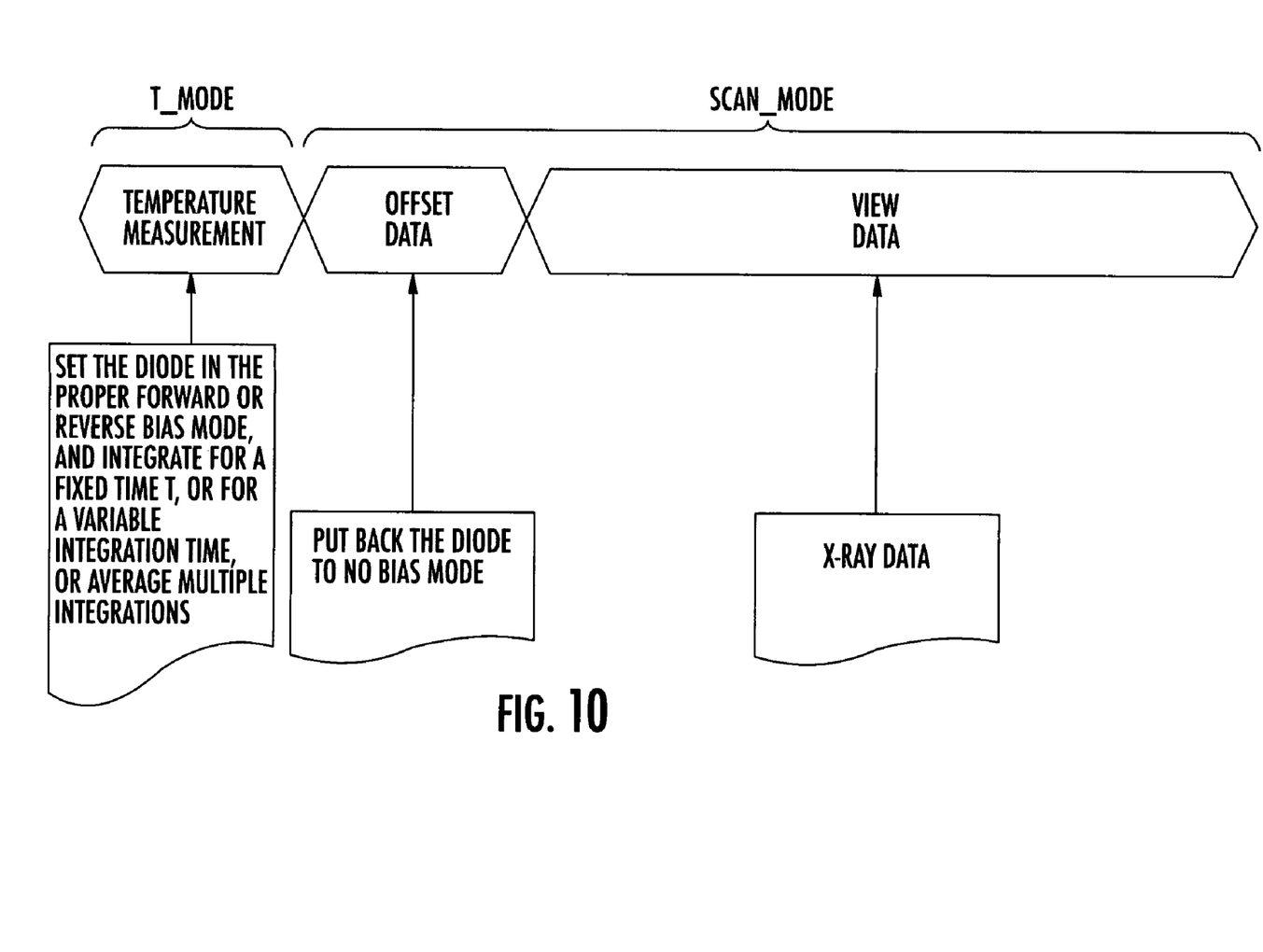
FIG. 10 illustrates an example algorithm for measuring the temperature vector in the beginning of the scan.

FIG. 9 illustrates an imaging system 10 with an associated display 20. Imaging system 10 can be of any modality, but in one embodiment, system 10 is a CT system. In another embodiment, system 10 is a dual modality imaging system such as a combined CT/PET. Display 20 can be separate from system 10 or integrated with system 10. System 10 includes an acquisition device such as an x-ray radiation detector, a Gamma Camera, an ultrasound probe and/or an MRI coil. In all the above modalities, please note that there is energy traveling at least partially through at least one component of a body and impinging an energy detector. A computer is coupled to the detector for processing the received data and producing an image if desired. The energy detector may include diodes as described herein.

Of course, the methods described herein are not limited to practice in system 10 and can be utilized in connection with many other types and variations of imaging systems. Although the herein described methods are described in a human patient setting, it is contemplated that the benefits of the invention accrue to non-human imaging systems such as those systems typically employed in small animal research. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Technical effects include that the herein described methods and apparatus allow many advantages gained by making measurements of the temperatures for every pixel. The advantages include the following:

1—Creation of a calibration vector relaxes the thermal management control in the detector.

2—Creation of a calibration vector relaxes the requirements of the scintillating pack with respect to temperature drift. This vector will be used to compensate for the gain drift due to temperature drift.

3—Creation of a calibration vector relaxes the requirements of the diode array (backlit diode) with respect to temperature drift. This vector can be used to compensate for the gain drift due to temperature drift.

4—The time required to warm-up the detector is reduced.

5—The gain drift due to thermal variation is correctable.

6—Improved Image Quality is provided. And

7—Improved inventory carry value (ICV) is provided by reducing the cost of the components and their processes.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method comprising creating a lookup table for thermal correction of an x-ray detector on a pixel by pixel basis, wherein the detector comprises a plurality of backlit diodes, wherein the lookup table was created by measuring the temperature of the diodes before a scan, and wherein the temperature was measured by reverse biasing the diodes.

2. A method in accordance with claim 1 further comprising correcting an image to at least partially remove artifacts from temperature drift.

3. A method comprising creating a lookup table for thermal correction of an x-ray detector on a pixel by pixel basis, wherein the detector comprises a plurality of backlit diodes, wherein the lookup table was created by measuring the temperature of the diodes before a scan, and wherein the temperature was measured by forward biasing the diodes.

4. A system comprising:
an energy source;
an energy detector positioned to receive energy emitted from said source, said energy detector comprising a plurality of diodes; and
a computer coupled to said detector, said computer configured to store a lookup table for thermal correction of said detector on a diode by diode basis, wherein the lookup table was created by measuring the temperature of the diodes, and wherein the temperature was measured by reverse biasing the diodes.

5. A system in accordance with claim 4 wherein said computer is further configured to correct an image to at least partially remove artifacts from temperature drift.

6. A system in accordance with claim 4 wherein said detector comprises a plurality of backlit diodes.

7. A system in accordance with claim 4 wherein the lookup table was created by measuring the temperature of the diodes before a scan.

8. A system comprising:
an energy source;
an energy detector positioned to receive energy emitted from said source, said energy detector comprising a plurality of diodes; and
a computer coupled to said detector, said computer configured to store a lookup table for thermal correction of said detector on a diode by diode basis wherein the temperature was measured to create the lookup table by forward biasing the diodes.

* * * * *